(12) United States Patent
John et al.

(10) Patent No.: US 9,675,699 B2
(45) Date of Patent: Jun. 13, 2017

(54) COOLING ENHANCING COMPOSITIONS

(71) Applicant: International Flavors & Fragrances Inc., New York, NY (US)

(72) Inventors: Thumpalasseril V. John, Morganville, NJ (US); Mark L. Dewis, Matawan, NJ (US); Kathryn Bardsley, Howell, NJ (US); Kenneth J. Kraut, Union Beach, NJ (US); Hou Wu, East Brunswick, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 13/723,791

(22) Filed: Dec. 21, 2012

(65) Prior Publication Data

US 2014/0219930 A1    Aug. 7, 2014

Related U.S. Application Data

(60) Provisional application No. 61/579,177, filed on Dec. 22, 2011.

(51) Int. Cl.
| | | |
|---|---|---|
| *A61K 47/22* | (2006.01) | |
| *A61K 8/37* | (2006.01) | |
| *A61K 8/34* | (2006.01) | |
| *A61K 8/42* | (2006.01) | |
| *A61K 8/49* | (2006.01) | |
| *A61Q 11/00* | (2006.01) | |
| *A23G 4/06* | (2006.01) | |
| *A23L 1/22* | (2006.01) | |
| *A23L 1/226* | (2006.01) | |
| *A61Q 19/00* | (2006.01) | |
| *A23L 27/00* | (2016.01) | |
| *A23L 27/10* | (2016.01) | |
| *A23L 27/20* | (2016.01) | |

(52) U.S. Cl.
CPC .............. *A61K 47/22* (2013.01); *A23G 4/06* (2013.01); *A23L 27/11* (2016.08); *A23L 27/2052* (2016.08); *A23L 27/88* (2016.08); *A61K 8/34* (2013.01); *A61K 8/37* (2013.01); *A61K 8/42* (2013.01); *A61K 8/498* (2013.01); *A61Q 11/00* (2013.01); *A61Q 19/00* (2013.01); *A23V 2002/00* (2013.01); *A61K 2800/244* (2013.01)

(58) Field of Classification Search
None
See application file for complete search history.

(56) References Cited

U.S. PATENT DOCUMENTS

| | | | |
|---|---|---|---|
| 4,983,378 A | 1/1991 | Parnell | 424/48 |
| 5,009,893 A | 4/1991 | Cherukuri et al. | |
| 6,497,234 B1 | 12/2002 | Coy-Herbert | 131/352 |
| 7,189,760 B2 | 3/2007 | Erman et al. | 514/529 |
| 8,685,436 B2 | 4/2014 | Ley et al. | 424/439 |
| 2002/0188019 A1 | 12/2002 | Ley et al. | |
| 2006/0251731 A1 | 11/2006 | Marchioni | 424/618 |
| 2007/0148283 A1 | 6/2007 | Harvey et al. | |
| 2008/0317923 A1* | 12/2008 | Ley | A23L 1/22 426/535 |
| 2010/0233102 A1 | 9/2010 | Krammer et al. | 424/54 |
| 2010/0292175 A1 | 11/2010 | Wessjohann et al. | 514/23 |
| 2011/0293538 A1* | 12/2011 | Ley et al. | 424/49 |

FOREIGN PATENT DOCUMENTS

| | | |
|---|---|---|
| DE | 2 203 947 | 8/1972 |
| EP | 1258200 B1 | 4/2002 |
| EP | 1 977 655 | 3/2008 |
| EP | 2 253 226 | 5/2010 |
| EP | 2 633 885 | 3/2012 |
| EP | 2 368 442 | 12/2014 |
| EP | 2 606 746 B1 | 9/2015 |
| WO | WO 2007/014879 A1 | 2/2007 |
| WO | WO 2008/124667 A1 | 10/2008 |
| WO | 2008/141333 | 11/2008 |
| WO | 2009/049800 | 4/2009 |
| WO | 2009/051632 | 4/2009 |
| WO | WO 2011/090709 A1 | 7/2011 |

OTHER PUBLICATIONS

MDC Examples of Natural Products—35 USC 101, Guidance from Dec. 2014.*
Arctander, Steffen; Perfume and Flavour Chemicals, 1969, vol. II, Item No. 1840.

* cited by examiner

*Primary Examiner* — Frederick Krass
*Assistant Examiner* — Michael P Cohen
(74) *Attorney, Agent, or Firm* — Licata & Tyrrell P.C.

(57) ABSTRACT

The following invention relates to a taste enhancer and a method of enhancing taste. The invention relates the use of a cooling enhancing composition which provides cooling enhancement when combined with other cooling compounds.

1 Claim, No Drawings

COOLING ENHANCING COMPOSITIONS

RELATED APPLICATION

This application claims the benefit of priority from U.S. Provisional Application Ser. No. 61/579,177, filed Dec. 22, 2011, the content of which is herein incorporated by reference in its entirety.

FIELD OF THE INVENTION

The following invention relates to a taste enhancer and a method of enhancing taste. The invention relates the use of a cooling enhancing composition which provides cooling enhancement when combined with other cooling compounds.

BACKGROUND OF THE INVENTION

A significant number of compounds are known to be useful in providing a cooling sensation in the mouth, in the nasal cavity and/or on skin. The best known and most widely used of these is menthol which in addition to olfaction caused a cooling response on cold receptors in the oral cavity, the nasal cavity and on skin.

In the field of flavors and fragrances for consumer products such as foodstuffs, beverages, tobacco products and personal care products there has always been great interest in compounds having a physiological cooling activity on the nervous system of the body, especially of the skin and the mucosa of the oral cavity, similar to that obtained with menthol.

Such compounds may be added to ingestible preparations, to tobacco products, and/or to products applied to the skin, for the purpose of stimulating the cold receptors of the nervous system in the surface tissues of the mucosa of the oral cavity or the skin, thereby creating a sensation of coolness and/or freshness in the mouth or on the skin.

Menthol has been used extensively for this purpose, and mainly as a fortifier for peppermint flavours (see "Perfume and Flavour Chemicals, Volume II, by Steffen Arctander, published 1969, Item No. 1840) but also in trace amounts in imitation butter, caramel, fruit complexes and licorice flavourings. Menthol is well known for its physiological cooling effect on the skin and mucous membranes of the mouth and has been extensively used as a flavouring agent (menthol being a major constituent of oil of peppermint) in foodstuffs, beverages, dentifrices, mouthwashes, etc. and as a component in a wide range of toiletries, liniments and lotions for topical application. Menthol is also a well known tobacco additive for producing a "cool" sensation in the mouth when smoking.

It is well established that the "cooling" effect of menthol is a physiological effect due to the direct action of menthol on the nerve endings of the human body responsible for the detection of hot or cold and is not due to latent heat of evaporation. It is believed that the menthol acts as a direct stimulus on the cold receptors at the nerve endings which in turn stimulate the central nervous system.

Although menthol is well established as a physiological coolant, its use in some compositions is impaired by its strong minty odour and its relative volatility.

A variety of compounds are known which provide a cooling sensation when ingested or contacted with the body. Perhaps the best known of these compounds is menthol. It is believed that menthol acts on the cold receptors at the nerve endings in order to provide this cooling effect.

Since menthol has a strong minty odor and high relative volatility, several other coolant compounds have been developed and reported in the technical literature as potential flavorants or odorants in a variety of topical and ingestible compositions. For example, U.S. Pat. No. 5,009,893 proposes the use of menthol in combination with N-substituted-p-menthane carboxamide compounds as coolant compositions in edible products.

Thus, varieties of compounds are known which provide cooling properties and are useful in a wide variety of products. However, there is still a need to provide coolant compositions having an improved cooling effect and/or taste perception.

SUMMARY OF THE INVENTION

Accordingly, it is an object of the present invention to provide improved coolant compositions.

It is a further object of the present invention to provide coolant compositions having a unique cooling sensation and taste perception.

It is a still further object of the present invention to provide coolant compositions including one or more cooling agents and a cooling enhancing composition which provide a complementary cooling sensation and taste perception.

The present invention relates to a composition selected from topical products, oral care products, nasal care products, toilet articles, ingestible products and chewing gum, which comprises a product base and an effective amount of a cooling compound selected and a coolant selected from the group consisting of menthol, WS3, WS5, WS23, menthyl glutarate, menthyl lactate and a cooling enhancing composition comprising eriodictyol, homoeriodictyol, hesperetin and mixtures thereof.

In a second aspect, the present invention relates to a composition including a coolant selected from the group consisting of menthol, WS3, WS5, WS23, menthyl glutarate, menthyl lactate and a cooling enhancing composition comprising eriodictyol, homoeriodictyol, hesperetin and mixtures thereof selected from the group of flavors, flavoring oils and herbal oils.

The present invention also relates to coolant compositions which include a primary cooling compound selected from the group consisting of menthol, WS3, WS5, WS23, menthyl glutarate, menthyl lactate and at least one secondary coolant component selected from the group consisting of menthol, WS3, WS5, methyl glutarate and a cooling enhancing composition comprising eriodictyol, homoeriodictyol, hesperetin and mixtures thereof.

DETAILED DESCRIPTION OF THE INVENTION

The present invention can be understood more readily by reference to the following detailed description of various embodiments of the invention and the Examples included therein and to the chemical drawings and Tables and their previous and following description. Before the present compounds, compositions, and/or methods are disclosed and described, it is to be understood that unless otherwise specifically indicated by the claims, the invention is not limited to specific foods or food preparation methods, specific comestibles or pharmaceutical carriers or formulations, or to particular modes of formulating the compounds of the invention into ingestible products for humans and animals or compositions intended for oral administration, because as one of ordinary skill in relevant arts is well aware, such things can of course, vary. It is also to be understood that the terminology used herein is for the purpose of describing particular embodiments only and is not intended to be limiting.

Definitions

A "comestibly, biologically or medicinally acceptable carrier or excipient" is a solid or liquid medium and/or composition that is used to prepare a desired dosage form of the inventive compound, in order to administer the inventive compound in a dispersed/diluted form, so that the biological effectiveness of the inventive compound is maximized. A comestibly, biologically or medicinally acceptable carrier includes many common food ingredients, such as water at neutral, acidic, or basic pH, fruit or vegetable juices, vinegar, marinades, beer, wine, natural water/fat emulsions such as milk or condensed milk, edible oils and shortenings, fatty acids, low molecular weight oligomers of propylene glycol, glyceryl esters of fatty acids, and dispersions or emulsions of such hydrophobic substances in aqueous media, salts such as sodium chloride, wheat flours, solvents such as ethanol, solid edible diluents such as vegetable powders or flours, or other liquid vehicles; dispersion or suspension aids; surface active agents; isotonic agents; thickening or emulsifying agents, preservatives; solid binders; lubricants and the like.

A cooling enhancing composition refers to a composition comprising eriodictyol, homoeriodictyol, hesperetin and mixtures thereof.

In addition, an "effective amount" is meant a level or amount of cooling composition in a material at which the incorporated composition exhibits a sensory effect.

A "flavor" herein refers to the perception of taste and/or smell in a subject, which include sweet, sour, salty, bitter, umami, and others. The subject may be a human or an animal.

A "flavoring agent" herein refers to a compound or a biologically acceptable salt thereof that induces a flavor or taste in an animal or a human.

A "flavor modifier" herein refers to a compound or biologically acceptable salt thereof that modulates, including enhancing or potentiating, and inducing, the tastes and/or smell of a natural or synthetic flavoring agent in an animal or a human.

A "flavor enhancer" herein refers to a compound or biologically acceptable salt thereof that enhances the tastes or smell of a natural or synthetic flavoring agent.

As used herein, the term "medicinal product" includes both solids and liquid compositions which are ingestible non-toxic materials which have medicinal value or comprise medicinally active agents such as cough syrups, cough drops, aspirin and chewable medicinal tablets.

An oral hygiene product includes solids and liquids such as toothpaste or mouthwash.

Menthol exists abundantly in nature and has been known for a long time as a physiological cooling compound. It is well-established that the "cooling" effect of menthol is a physiological effect. Menthol has been used widely in cigarettes, cosmetics, toothpastes, chewing gum, sweets, and medicines. Disadvantages of menthol include its strong "stinging" smell, bitter taste, burning sensation in high concentration and high volatility. These undesirable properties limit applications of menthol to some extent. Substitutes of menthol have been actively sought. One class of suitable substitutes include the ester coolers, i.e., esters which exhibit a physiological cooling effect.

The following are the typical applications and use levels for menthol. The maximum use level of menthol is dependent on the application. Typical applications consist of alcoholic beverages, baked goods, chewing gum, frozen dairy, gelatin pudding, hard candy, non-alcoholic beverages and soft candy. The average use levels and maximum use levels as follows:

Gum—from about 0.2% to about 1.5% (could include core and coating in a pellet).

HBC—from about 0.05% to about 0.2% (Includes dosage amount for cough suppressant)

Chews—from about 0.05 to about 0.12%

Alcoholic Beverages from about 1 ppm to about 60 ppm

Baked Goods from about 5 ppm to about 90 ppm

Frozen Dairy from about 5 ppm to about 70 ppm

Gelatin Pudding from about 2 ppm to about 25 ppm

Non-Alc Beverages from about 0.1 ppm to about 10 ppm

In addition to (−)-menthol, it is contemplated that other cooling agents can be used as a point of reference. Moreover, it is contemplated that the reference can be arbitrarily selected at, e.g., 1,10, 100, 1000, etc.

In this regard, U.S. Patent Application No. 20050265930 teaches that with respect to WS-3, with a relative cooling strength of 10.0, the relative cooling strength of highly purified WS-5 is about 16.7; WS-23 is about 5.0; Menthyl Lactate is about 2.9; WS-14 is about 5.0; WS-30 is about 1.5; N,2,2,6-Tetramethylcyclohexane-l-carboxamide is about 1.0; and monomenthyl glutarate is about 3.5.

Measurement of the cooling strength of one or more agents identified in accordance with the present method can be achieved using conventional methods. See, e.g., U.S. Patent Application No. 20050265930. By way of illustration, aqueous solutions of the cooling agent(s) are prepared, wherein each solution contains, e.g., 10 ppm of cooling agent(s). The solutions are organoleptically tested using a scale from, e.g., 0 (zero) to 100 of the cooling strength in comparison with the standard solution of 10 ppm of (−)-menthol, which is assigned a score of 100.

Surprisingly, it has been found that the cooling enhancing composition of the present invention, even at very low concentrations, can enhance the cooling taste impression of a multiplicity cooling substances also known as coolers, in particular of menthol, WS3, WS5, WS23, menthyl glutarate and menthyl lactate.

In a preferred embodiment of the invention, a composition is provided which is selected from topical products for humans and animals, oral care products, nasal care products, and chewing gum which comprises a product base and an effective amount of a coolant selected from the group consisting of menthol, WS3, WS5, WS23, menthyl glutarate, menthyl lactate and a cooling enhancing composition comprising eriodictyol, homoeriodictyol, hesperetin and mixtures thereof. The amounts of cooling enhancement composition may be adjusted based on the end use application and the amount of the other cooler used in the application.

The invention further relates to topical products for humans and animals, oral care products, nasal care products, and chewing gum characterized in that they have an active content of eriodictyol, homoeriodictyol, hesperetin and mixtures thereof or their mixtures.

They generally comprise 0.000001% by weight to 10% by weight, preferably 0.00001% to 1% by weight, but more preferably 0.0001% by weight to 0.1% by weight, based on the total weight of the preparation, of cooling enhancing compositions containing eriodictyol, homoeriodictyol, hesperetin and mixtures thereof or their mixtures.

Other customary active compounds, base compounds, aids and additives for food consumed for nutrition or pleasure or oral pharmaceutical preparations can be present in amounts of 5 to 99.999999% by weight, preferably 10 to 80% by weight, based on the total weight of the preparation. In addition, the preparations can comprise water in an amount up to 99.999999% by weight, preferably 5 to 80% by weight, based on the total weight of the preparation.

The cooling enhancing compositions generally comprise 0.0001% by weight to 95% by weight, preferably 0.1 to 80% by weight, but in particular 1% by weight to 50% by weight, based on the total weight of the preparation, of eriodictyol, homoeriodictyol, hesperetin and mixtures thereof or their mixtures.

In another embodiment a composition is provided which may contain menthol and a cooling enhancing composition comprising eriodictyol, homoeriodictyol, hesperetin and mixtures thereof.

In another embodiment a composition is provided which may contain WS3 and a cooling enhancing composition comprising eriodictyol, homoeriodictyol, hesperetin and mixtures thereof.

In yet another embodiment a composition is provided which may contain WS5 and a cooling enhancing composition comprising eriodictyol, homoeriodictyol, hesperetin and mixtures thereof.

In another embodiment a composition is provided which may contain WS23 and a cooling enhancing composition comprising eriodictyol, homoeriodictyol, hesperetin and mixtures thereof.

In still another embodiment a composition is provided which may contain menthyl glutarate and a cooling enhancing composition comprising eriodictyol, homoeriodictyol, hesperetin and mixtures thereof.

In yet another embodiment a composition is provided which may contain menthyl lactate and a cooling enhancing composition comprising eriodictyol, homoeriodictyol, hesperetin and mixtures thereof.

In yet another embodiment a composition is provided which may contain an ingestible product for humans or animals which comprises a product base selected from the group consisting of baked goods, dairy products, fruit ices, confectionery products, sugarless candies, jams, jellies, gelatins, puddings, animal feeds, pressed confectionery tablets, hard-boiled candies, pectin-based candies, chewy candies, creme-centered candies, fondants, sugarless hard-boiled candies, sugarless pectin-based candies, sugarless chewy candies, sugarless creme-centered candies, toothpastes, mouthwashes, breath fresheners, carbonated beverages, mineral waters, powdered beverage mixes, other non-alcoholic beverages, cough drops, lozenges, cough mixtures, decongestants, anti-irritants, antacids, anti-indigestion preparations and oral analgesics, and an effective amount of a coolant selected from the group consisting of menthol, WS3, WS5, methyl glutarate and a cooling enhancing composition comprising eriodictyol, homoeriodictyol, hesperetin and mixtures thereof.

In more preferred embodiment the ingestible product for humans or animals is a food, beverage, or oral hygiene product.

In yet a further embodiment the food or beverage product is selected from the group consisting of confectioneries, bakery products, dairy products, meal replacement products, soup products, dehydrated and culinary food, frozen food, canned food, snack food, baby food product, oils and fats, and seasonings or seasoning blends.

In still another embodiment the cooling enhancing composition in the ingestible product for humans or animals is present in the one ingestible product at a concentration from about 0.0001 ppm to about 500 ppm, based on the total weight of said product, more preferably from about 0.0005 ppm to about 50 ppm, based on the total weight of said product, more preferably from about 0.001 ppm to about 10 ppm and even more preferably from about 0.002 ppm to about 5 ppm concentration from about 0.01 ppm to about 30 ppm.

In another embodiment a method for enhancing the cooling sensation of a comestible or medicinal product comprising: a) providing at least one ingestible product for humans or animals, and b) combining the ingestible product with at least an effective amount of a cooler and an effective amount of a cooling enhancing composition comprising eriodictyol, homoeriodictyol, hesperetin and mixtures thereof.

Accordingly, the one ingestible product is a food, beverage, or oral hygiene product wherein the food or beverage product is selected from the group consisting of confectioneries, bakery products, dairy products, meal replacement products, soup products, dehydrated and culinary food, frozen food, canned food, snack food, baby food product, oils and fats, and seasonings or seasoning blends.

According to the method the cooling enhancing composition is present in the one ingestible product at a concentration from about 0.0001 ppm to about 500 ppm, based on the total weight of said product, more preferably from about 0.0005 ppm to about 50 ppm, based on the total weight of said product, more preferably from about 0.001 ppm to about 10 ppm and even more preferably from about 0.002 ppm to about 5 ppm.

The composition according to the present invention may suitably be prepared in the form of a liquid, a paste or a powder, further comprising a carrier material, such as maltodextrin, modified starch, gum Arabic, ethanol or propylene glycol.

In case the composition is a flavor composition it is particularly preferred that the composition is a free flowing powder. Typically such flavor compositions comprise a food grade carrier material. i.e. a carrier material which is non-toxic and does not significantly affect the organoleptic properties of the combination of the cold receptor stimulant and the one or more flavour imparting substances.

According to another particularly preferred embodiment of the invention said consumer product is a foodstuff selected from the group of confectioneries, including hard and soft candies, chewing gum, edible films, lozenges and pastilles, desserts and ice cream; a beverage selected from the group of soft drinks, alcoholic beverages and dairy drinks; an oral care product selected from the group of toothpastes, mouthwashes, dental floss, anti-plaque and anti-gingivitis compositions; a personal care product selected from the group of deodorants, shampoos, skin sanitizing compositions, lotions and shaving products; or a tobacco product selected from the group of smoking tobacco, chewing tobacco as well tobacco substitute products.

In accordance with a particularly preferred embodiment of the invention, a consumer product as defined herein before is provided, wherein said consumer product further comprises at least one, preferably at least two, most preferably at least three other flavor imparting substances or fragrance imparting substances as defined herein before.

The relative amounts of the cooler and cooling enhancing composition of the present invention may be varied over a wide range of compositions depending upon the particular flavor desired. Other potential combinations of the primary coolant with secondary coolant components will be apparent to the man of skill in the art.

Typically, the coolant compositions are made by mixing the primary and secondary coolants together in a conventional manner.

The invention is described in greater detail by the following non-limiting examples.

EXAMPLE A

Preparation of the Cooling Enhancing Composition

The cooling enhancing composition was prepared according to the following process: 300 g of Eriodictyon californicum (California Yerba Santa) leaves was extracted with 2500 ml ethyl alcohol 2 times at 60° C. for 3 hours each. The extract were drained and combined.

The above combined extract was concentrated under reduced pressure at 40° C. to get the concentrate (90 to 110 g)

The above concentrate was mixed with 800 ml ethyl acetate and refrigerated (4° C.) overnight and then filtered to remove wax. The filtrate was mixed with 800 ml water containing 40 g NaOH and refrigerated (4° C.) for 2 days.

The above refrigerated liquid was transferred into a separatory funnel and left undisturbed to obtain 2 layers. The bottom (water) layer was drained and filtered and the residue was collected.

The above residue was then dissolved in 500 ml hot water.(If needed heat to completely solubilize.) The pH of the solution is adjusted to 6.5 with 10% H3PO4. (The pH should be less than 7.) The liquid is then cooled and filtered. The thus obtained residue is dried to get the final product (4.5 to 11 g)

The composition of the product contains 86 to 93% homoeriodictyol, 1-4% hesperetin and 0.1 to 1% eriodictyol

EXAMPLE B

Preparation of the Cooling Enhancing Composition
Details from batch: FPP-11-483-3-1

The cooling enhancing composition was prepared according to the following process: 4 kg of Eriodictyon californicum (California Yerba Santa) leaves were extracted with ethyl acetatel 2 times at 45° C. for 3 hours each. The first extraction used 4:1 solvent to leaves and the second used 3:1. The extracts were drained, combined and filtered.

The above combined extract was concentrated under reduced pressure at 45° C.-50° C. to get the concentrate (approximately 1× the botanical charge). The concentrate was then chilled to 5C for 16 hours and filtered to remove wax.

The filtrate was mixed 1:1 filtrate to 5% NaOH solution and chilled to 5C for 48 hours until the pH was below 10.

The above refrigerated liquid was filtered to recover solid precipitate which formed.

The solids were dissolved in 50C water (about 9x their weight). The pH of the solution was adjusted to 6.5 with H3PO4. The liquid is then cooled and filtered. The obtained residue was dried to get the final product (approximately 3.15% yield on the botanical charged).

The composition of the product contains 74% homoeriodictyol, 3.85% hesperetin and 0.89% eriodictyol.

EXAMPLES I

Responsible actives were determined by comparing the cooling profile of menthol alone (the control) against the solutions with either menthol or cooling enhancing compositions or menthol with the active(s). The profile attributes consist of onset, location, intensity and duration of cooling.

1) Formulation:
Control: 5mg menthol/1 Liter of water (=5 ppm)

The use level of 5 ppm is a standard use level within our research facility when looking for cooling enhancement. The levels of the actives were determined after tasting them at varying concentrations within the range of 1 ppm to 200 ppm. The levels presented were deemed to be optimal by offering the greatest functionality.

The cooling enhancing compositions listed below were dosed on top of the menthol control.

Cooling Enhancing Composition

| | Concentrations (%, wt/wt) | | |
|---|---|---|---|
| Samples | eriodictyol | homoeriodictyol | hesperetin |
| Cooling Enhancing Composition | 0.93 | 89.70 | 3.41 |

5 mg menthol/1 Liter of water (=5 ppm)
Eriodictyol, Sigma-Aldrich 95% Pure
 50 mg menthol/1 Liter of water (=50 ppm)
Hespereitin, Sigma-Aldrich, 95% Pure
 50 mg menthol/1 Liter of water (=50 ppm)
Luteolin, Sigma-Aldrich 98% Pure
 50 mg menthol/1 Liter of water (=50 ppm)
Inherent Cooling of Materials (In Water):

The cooling enhancing composition was tasted at 200 ppm, 50 ppm and 25 ppm in water and cooling was not observed.

Eriodityol was tasted alone in water at 35 ppm; slight irritation (piperin-like burn) without cooling was observed.
Homoeriodictyol:
 5 ppm—taste neutral, slightly drying, no cooling
 25 ppm—drying, not cooling
 Luteolin, 50 ppm—slightly stale flavor, no cooling
Enhancement Observed with Other Coolers
Menthol
 Menthol dosed at 5 ppm is equivalent to Menthol dosed at 4 ppm+cooling enhancing composition @ 1 ppm (a 20% enhancement)
 Menthol dosed at 5 ppm is equivalent to Menthol dosed at 2.5 ppm+cooling enhancing composition at 10 ppm (a 50% enhancement)
 Menthol dosed at 5 ppm is equivalent to Menthol dosed at 2 ppm+cooling enhancing composition at 20 ppm (a 60% enhancement)
WS3
 WS3 dosed at 5 ppm is equivalent to WS3 dosed at 4 ppm+cooling enhancing composition @ 1 ppm (a 20% enhancement)
 WS3 dosed at 5 ppm is equivalent to WS3 dosed at 4 ppm+cooling enhancing composition dosed at 10 ppm (a 20% enhancement)
 WS3 dosed at 5 ppm is equivalent to WS3 dosed at 4 ppm+cooling enhancing composition dosed at 20 ppm (a 20% enhancement)
WS5
 WS5 dosed at 3.5 ppm is equivalent to WS5 dosed at 2.5 ppm+cooling enhancing composition dosed at 1 ppm (a 29% enhancement)
 WS5 dosed at 4 ppm is equivalent to WS5 dosed at 2.5 ppm+cooling enhancing composition dosed at 10 ppm (a 40% enhancement)

WS5 dosed at 4 ppm is equivalent to WS5 dosed at 2.5 ppm+cooling enhancing composition dosed at 20 ppm (a 40% enhancement)

WS23

WS23 dosed at 16.25 ppm is equivalent to WS23 dosed at 15 ppm+cooling enhancing composition at 1 ppm (a 7.7% enhancement)

WS23 dosed at 17.5 ppm is equivalent to WS23 dosed at 15 ppm+cooling enhancing composition at 10 ppm (a 14.3% enhancement)

WS23 dosed at 17.5 ppm is equivalent to WS23 dosed at 15 ppm+cooling enhancing composition at 20 ppm (a 14.3% enhancement)

Menthol Glutarate

Menthyl Glutarate dosed at 18 ppm is equivalent to Menthyl Glutarate dosed at 15 ppm+cooling enhancing composition dosed at 1 ppm (a 16.7% enhancement)

Menthyl Glutarate dosed at 20 ppm is equivalent to Menthyl Glutarate dosed at 15 ppm+cooling enhancing composition dosed at 10 ppm (a 25% enhancement)

Menthyl Glutarate dosed at 20 ppm is equivalent to Menthyl Glutarate dosed at 15 ppm+cooling enhancing composition dosed at 20 ppm (a 25% enhancement)

Menthyl Lactate

WS3 dosed at 11 ppm is equivalent to Menthyl Lactate @ 10 ppm+cooling enhancing composition at 1 ppm (a 9% enhancement)

WS3 dosed at 11ppm is equivalent to Menthyl Lactate @ 10 ppm+cooling enhancing composition at 10 ppm (a 9% enhancement)

WS3 dosed at 12 ppm is equivalent to Menthyl Lactate @ 10 ppm+cooling enhancing composition at 20 ppm (a 16.7% enhancement)

EXAMPLE II

The results below were obtained by a group of five trained panelists.)

5 ppm Menthol:

Taste Descriptors: thin and moderate cooling, slight burn, some bitterness, cooling on front, tip of tongue and gums, mild cooling on breath-in, slightly harsh and sharp.

5 ppm Menthol+5 ppm Cooling Enhancing Composition (Extract of Yerba Santa):

Taste Descriptors: faster onset of cooling, more intense, no bitter burn, clean, strong cooling sensation on gums and throat, more delocalized cooling on center of tongue including the back of throat, cooling intensity is longer lasting.

Average Increase: 97%

5 ppm Menthol+5 ppm Homoeriodictyol:

Taste Descriptors: faster onset of cooling than menthol alone, cooling localized on front of tongue, cold as in temperature, slight teeth cooling, fully delocalized cooling after 10 seconds reaching back of throat and roof of mouth, mild cooling on breath-in, diminished menthol burn.

Average Increase: 66%

5 ppm Menthol+50 ppm Eriodictyol:

Taste Descriptors: Cooling localized on middle of tongue stronger than control, more intense in back of throat on breath-in, does not trigger a faster onset, cooling builds more after expectorating and on breath-in, sharpened the intensity of cooling in the center and sides of tongue and roof of mouth.

Average Increase: 56%

5 ppm Menthol+50 ppm Hesperetin:

Taste Descriptors: Sweet, no impact on cooling, slightly bitter, drying, cooling is delocalized and about the same strength as control.

Average Increase: 0%

5 ppm Menthol+50 ppm Luteolin:

Taste Descriptors: Equivalent cooling as compared to control, localized on front tip of tongue, gums and roof of mouth, did not expedite onset but smoothed upfront mouthfeel, slight irritation to tongue and back of mouth/ throat cavity.

Average Increase: 32%

5 ppm Menthol+4.485 ppm Homoeriodictyol+0.0465 ppm Eriodictyol+0.0465 ppm Luteolin:

Taste Descriptors: Faster onset, more intense, significant increase in cooling over control, fully delocalized, smooth, less burn, clean.

Average Increase: 85%

What is claimed:

1. A coolant composition consisting of (i) an effective amount of menthol; (ii) at least one of homoeriodictyol, eriodictyol or hesperetin; and (iii) a carrier material, wherein the amount of (ii) is effective to increase the cooling sensation of said menthol by 56 to 66%.

* * * * *